US006051756A

United States Patent [19]
Chen et al.

[11] Patent Number: 6,051,756
[45] Date of Patent: Apr. 18, 2000

[54] PARTICLE BOMBARDMENT TRANSFORMATION OF BRASSICA

[75] Inventors: Zhizheng Chen, Fort Collins, Colo.; Jennifer Celio, Carson City, Nev.

[73] Assignee: Cargill, Incorporated, Wayzata, Minn.

[21] Appl. No.: 09/031,178

[22] Filed: Feb. 26, 1998

[51] Int. Cl.[7] .............................. C12N 5/04; C12N 15/82; C12N 15/87; C12N 15/90; A01H 5/00
[52] U.S. Cl. ........................ 800/293; 435/320.1; 435/419; 435/430; 435/470; 800/285; 800/286; 800/298; 800/306
[58] Field of Search ................................ 435/69.71, 410, 435/419, 430, 470; 536/24.5; 800/278, 285, 286, 293, 295, 298, 306

[56] References Cited

U.S. PATENT DOCUMENTS

| 5,324,657 | 6/1994 | Tanny | 435/240.45 |
|---|---|---|---|
| 5,608,152 | 3/1997 | Kridl et al. | 800/205 |
| 5,736,369 | 4/1998 | Bowen et al. | 435/172.3 |

OTHER PUBLICATIONS

Chen et al., "A combined use of microprojectile bombardment and DNA inbibition enhances transformation frequency of canola (*Brassica napus L.*)," *Theor. Appl. Genet.* 88–187–192 (1994).
Comai et al., "Coordinate expression of transcriptionally regulated isocitrate lyase and malate synthase genes in *Brassica napus,*" *The Plant Cell* 1:293–300 (1989).
Goldberg et al., "Regulation of gene expression during plant embryogenesis," *Cell* 56:149–160 (1989).
Dunder et al., "Comparison of performance characteristics of different Biolistic® devices" in US/EG Bulletin 1689, BIO–RAD (best copy available).
Heiser W., "Optimization of Biolistic® transformation using the helium–driven PDS–1000/He system" US/EG Bulletin 1688, BIO–RAD (best copy available).
Higgins et al., "Synthesis and regulation of major proteins in seeds," *Ann. Rev. Plant Physiol.* 35:191–221 (1984).
Jefferson et al., "GUS fusions: β–glucuronidase as a sensitive and versatile gene fusion marker in higher plants," *EMBO J.* 6:3901–3907 (1987).
Klein T et al., "Transfer of foreign genes into intact maize cells with high–velocity microprojectiles," *Proc. Natl. Acad. Sci. U.S.A.* 85:4305–4309 (1988).
Klein T. et al., "Factors influencing gene delivery into a Zea Mays cells by high–velocity microprojectiles," *Bio/Technology* 6:559–563 (1988).
Lee et al., "Genomic nucleotide sequence of a *Brassica napus* 20–kilodalton oleosin gene," *Plant Physiol.* 96–1395–1397 (1991).
Lee et al., "Maize oleosin is correctly targeted to seed oil bodies in *Brassica napus* transformed with the maize oleosin gene," *Proc. Natl. Acad. Sci. USA* 88:181–6185 (1991).
Post–Beittenmiller et al., "DNA sequence of a genomic clone encoding an Arabidopsis acyl carrier protein (ACP)," *Nucl. Acids Res.* 17:1777 (1989).
Rose et al. "The nucleotide sequence of a cDNA clone encoding acyl carrier protein (ACP) from *Brassica campestris* seeds," *Nucl. Acids Res.* 15:7197 (1987).

Safford et al., "Plastid–localised seed acyl–carrier protein of *Brassica napus* is encoded by a distinct, nuclear multigene family," *Eur. J. Biochem.* 174:287–295 (1988).
Sanford et al., "Optimizing the biolistic process for different biological applications," *Methods Enzymol.* 217:483–509 (1993).
Sanford et al., "An improved, helium–driven biolistic device," *Technique* 3:3–16 (1991).
Sanford et al., "Delivery of substances into cells and tissues using a particle bombardment process," *J. Part. Sci. Technol.* 5:27–37 (1987).
Shanklin et al., "Stearoyl–acyl–carrier–protein desaturase from higher plants is structurally unrelated to the animal and fungal homologs," *Proc. Natl. Acad. Sci. USA* 88:2510–2514 (1991).
Siggaard–Andersen et al., "Primary structure of a cerulenin–binding β–ketoacyl–[acyl carrier protein] synthase from barley chloroplasts," *Proc. Natl. Acad. Sci. USA* 88:4114–4118 (1991).
Stomp, Anne–Marie, "Histochemical localization of β–glucuronidase," in Sean R. Gallagher (ed.), *GUS Protocols: Using the GUS Gene as a Reporter of Gene Expression*, pp. 103–113, Academic Press, San Diego, California, 1992.
Thompson et al., "Primary structures of the precursor and mature forms of stearoyl–acyl carrier protein desaturase from safflower embryos and requirement of ferredoxin for enzyme activity," *Proc. Natl. Acad. Sci. USA* 88:2578–2582 (1991).
Villemont et al., "Role of th host cell in the Agrobacterium–mediated genetic transformation of Petunia: evidence of an S–phase control mechanism for T–DNA transfer," *Planta*, 201:160–172 (1997).
Weising et al., "Foreign genes in plants: transfer, structure, expression, and applications," *Ann. Rev. Genetics* 22:421–477 (1988).
Seki et al, Plant Mol. Biol., vol. 17 pp. 259–263, 1991.
Radke et al, Plant Cell Rep., vol. 11, pp. 499–505, 1992.
Tabler et al, Gene, vol. 108, pp. 175–183, 1991.
Knutzon et al, Proc. Natl. Acad. Sci., USA, vol. 89, pp. 2624–2628, 1992.
Christou et al, Meth. Cell Biol., vo.. 50, pp. 375–382, 1995.
Fujimura et al, In Cell Culture and Somatic Cell Genetics of Plants, I.K. Vasil, Ed., Academic Press, Orlando FA, pp. 159–166, 1984.

*Primary Examiner*—Gary Benzion
*Assistant Examiner*—Ashwin D. Mehta
*Attorney, Agent, or Firm*—Fish & Richardson P.C., P.A.

[57] ABSTRACT

The invention involves methods and materials related to the transformation of Brassica by particle bombardment. Specifically, the invention provides methods of preparing non-embryo Brassica tissue such that Brassica cells are capable of being cultured, transformed by particle bombardment, and regenerated into plants. In addition, this invention provides stably transformed Brassica cells as well as their progeny. This invention also provides methods of culturing Brassica tissue with liquid medium such that transformed Brassica cells are identified and regenerated into transformed Brassica plants.

30 Claims, 1 Drawing Sheet

PARTICLE BOMBARDMENT TRANSFORMATION OF BRASSICA

BACKGROUND

1. Technical Field

The invention relates to methods and materials involved in the transformation of Brassica by particle bombardment.

2. Background Information

Brassica species include a large group of agriculturally important crops that are used by humans as vegetables, edible oils, and condiments. In fact, Brassica oil production accounts for more than 12 percent of the world's edible oil. To improve the quality of agriculturally important crops, cultivators have traditionally relied upon conventional breeding methods. With the current advances in plant molecular biology and genetics, however, cultivators can now improve plant quality through the introduction of foreign DNA.

Several different methods have been used to transform plants. One commonly used method involves bombarding plant cells with microparticles that have been coated with the DNA of interest. Indeed, particle bombardment methods have been widely used to transform corn, soybean, wheat, and rice. Attempts to transform Brassica species using particle bombardment, however, have not been as successful. In fact, the only successful transformation of Brassica required substantial manipulation of Brassica embryos. Thus, researchers currently rely on alternative approaches such as Agrobacterium-mediated methods to transform Brassica.

SUMMARY

The invention involves the transformation of Brassica species by particle bombardment. Specifically, the invention is based on the discovery of a quick and convenient tissue preparation technique that results in Brassica cells that are capable of being cultured, transformed by particle bombardment, and regenerated into plants. In addition, the invention provides transformed cells as well as regenerated plants that grow to maturity and set seeds. Such regenerated plants and their offspring stably express the transferred nucleic acid molecule. The simplicity of the invented method described herein makes particle bombardment transformation in Brassica not only possible, but also economically feasible.

One aspect of the invention provides a method of producing transformed Brassica cells involving bombarding cells prepared from non-embryo Brassica tissue with nucleic acid-coated microprojectiles and identifying cells transformed with the nucleic acid. Cells transformed with the nucleic acid can be identified by placing the bombarded cells onto a floatation device, contacting the floatation device with liquid selection medium, and selecting cells that survive. This method can also involve regenerating Brassica plants from the transformed cells. For example, identified cells can be placed onto a floatation device that contacts liquid regeneration medium. The cells prepared from non-embryo Brassica tissue can be diploid. In addition, the non-embryo Brassica tissue can be from a seedling, for example, a 4–6 day old sterile seedling. The cells can be prepared from non-embryo Brassica tissue by cutting the tissue into pieces and contacting the pieces with induction medium. For example, the cells can be prepared from non-embryo Brassica tissue by a method comprising cutting a hypocotyl from a seedling into multiple pieces, slicing the pieces longitudinally, and contacting the epidermal side of the longitudinal slices with induction medium. The cells can also be prepared from non-embryo Brassica tissue by a method comprising macerating the tissue into a cellular slurry. For example, the cells can be prepared from non-embryo Brassica tissue by a method comprising removing the lower portion of a hypocotyl from a seedling, combining the remaining upper portion, which contains a shoot tip, cotyledons, and 10–50 percent of the hypocotyl, with induction medium, and macerating the combination into a cellular slurry. In addition, the cellular slurry can also be enriched for 46–230 micron-sized cellular matter. The nucleic acid used to transform Brassica cells can regulate the expression of or encode a polypeptide. For example, the nucleic acid can encode an anti-sense molecule, such as a ribozyme or anti-sense oligonucleotide. Further, the Brassica tissue can be from Brassica species such as *Brassica napus, Brassica juncea, Brassica carinata, Brassica nigra, Brassica oleracea*, and *Brassica campestris* (also called "rapa").

Another aspect of the invention provides Brassica cells and progeny thereof produced by bombarding cells prepared from non-embryo Brassica tissue with nucleic acid-coated microprojectiles and identifying cells transformed with the nucleic acid.

Another aspect of the invention provides a method for culturing Brassica tissue involving placing Brassica tissue onto a floatation device that contacts liquid medium. This liquid medium can be selection medium. Culturing Brassica tissue on selection medium can result in the identification of Brassica tissue that has been transformed with nucleic acid. In addition, this liquid medium can be regeneration medium. Culturing Brassica tissue on regeneration medium can result in the regeneration of a Brassica plant from Brassica tissue.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
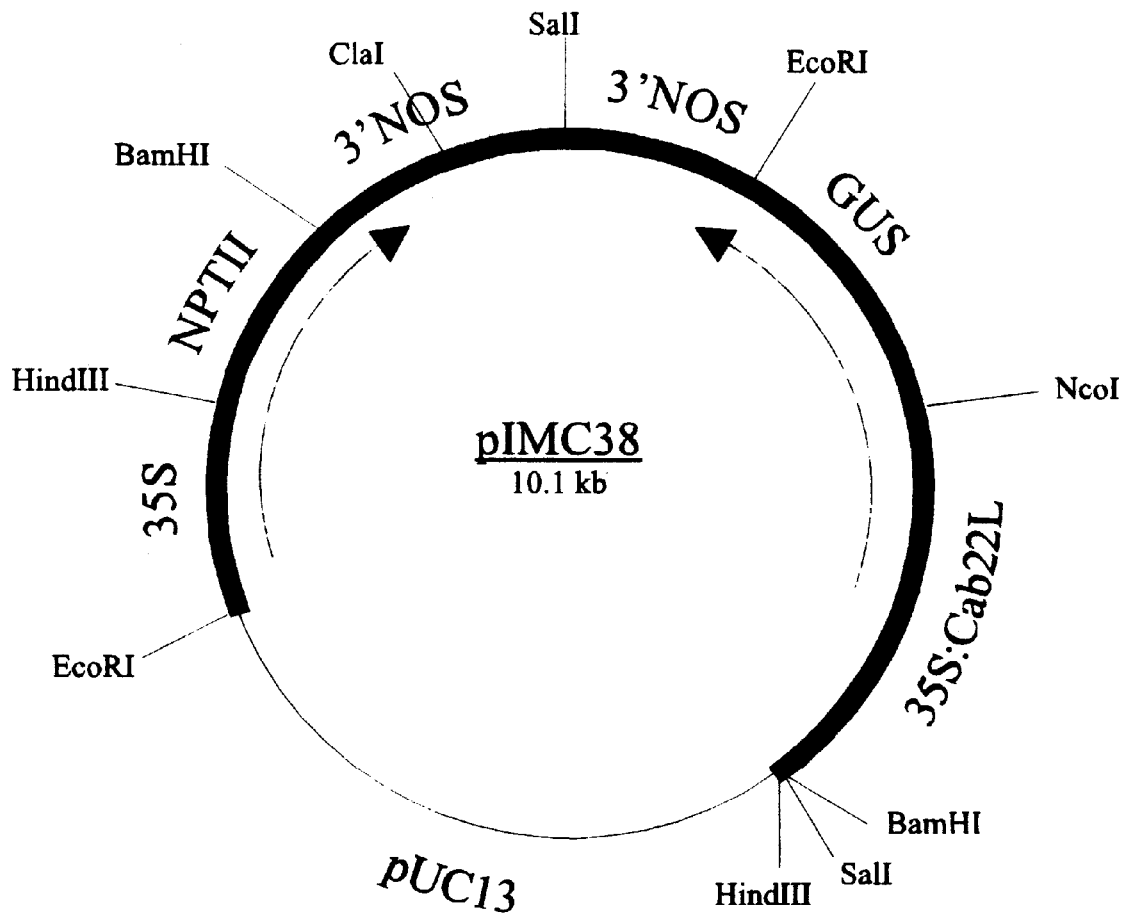
FIG. 1 is a diagram depicting the pIMC38 construct used in the experiments reported herein.

The invention provides methods and materials related to the transformation of Brassica by particle bombardment. Specifically, the invention provides methods of preparing non-embryo Brassica tissue such that Brassica cells are capable of being cultured, transformed by particle bombardment, and regenerated into plants. The invention also provides stably transformed Brassica cells as well as their progeny. Transformed plants are also referred to herein as transgenic plants.

Tissue Preparation

A cell or tissue preparation is defined as a group of cells or tissues arranged in a manner suitable for particle bombardment. To ensure successful transformation, the cell or tissue preparation provides a relatively large number of cells, preferably rapidly dividing cells, that are exposed at the surface such that they can receive nucleic acid coated particles. In addition, the recipient cells must be able to continue growing and to regenerate plants. A number of non-embryo Brassica cell or tissue sources can be used to prepare cell or tissue preparations that meet these criteria. For example, leaf protoplasts, isolated microspore cultures, stem tissues, and hypocotyl tissues derived from Brassica can be used as sources of Brassica cells. Using non-embryo tissue sources considerably simplifies transformation procedures. Typically, hypocotyl tissues prepared from young seedlings grown under sterile conditions are used. In this case, the hypocotyl can be cut into longitudinal slices. Alternatively, an upper portion of a seedling can be ground into a cellular slurry. Such an upper portion can include the two cotyledons, shoot tip, as well as the top section of the hypocotyl.

A cellular slurry is any liquid suspension of insoluble cellular matter that contains viable cells. A blender can be used to grind Brassica tissue into a cellular slurry. In addition, a cellular slurry can be sorted into groups based on the size of the insoluble cellular matter. For example, a cellular slurry can be sorted through a series of meshes such that insoluble cellular matter of a particular size is enriched. A cellular slurry of any size can be used for particle bombardment provided the cellular slurry contains viable cells. For example, a cellular slurry can be enriched for cellular matter about 35 microns to about 500 microns in size or about 46 microns to about 230 microns in size and used for particle bombardment.

The Brassica tissue preparations can contain diploid or haploid cells. When using diploid cells, it is understood that the resulting transformed cells will most likely be heterozygous at each integration site. In other words, it is extremely unlikely that a copy of the introduced nucleic acid will integrate into the same position on both chromosomes. When using haploid cells, however, the resulting transformed haploid cells can be treated with colchicine to induce chromosome doubling. Thus, the resulting cells will most likely be homozygous at each integration site. Alternatively, haploid plants can be regenerated from the resulting transformed haploid cells. These haploid plants then, in turn, can be crossed with other plants to produce plants that are either heterozygous or homozygous at particular integration sites. Further, cells that integrate an introduced nucleic acid sequence into their genome are called stably transformed cells. Stably transformed cells typically retain the introduced nucleic acid sequence with each cell division. Cells that contain introduced nucleic acid sequences that are not integrated into the genome are called transiently transformed cells. Transiently transformed cells typically lose some portion of the introduced nucleic acid sequence with each cell division. Thus, transformed cells can be either transiently and/or stably transformed.

A non-embryo Brassica tissue preparation can be cultured on induction medium before bombardment, e.g., a solid induction medium. Typically, solid medium is made from liquid medium by adding agar. Induction medium typically contains Murashige and Skoog (MS) medium as well as relatively higher concentrations of auxin, e.g., 2,4-dichlorophenoxyacetic acid (2,4-D), and relatively lower concentrations of cytokinin, e.g., kinetin. For example, 1 mg/L of 2,4-D and 0.3 mg/L kinetin can be added to MS medium and used. In addition, the tissue preparation is usually cultured on the induction medium for 1–3 days before bombardment.

For the purpose of this invention, solid and/or liquid tissue culture techniques can be used. For example, the induction, selection, and regeneration medium can be either in solid or liquid form. When using solid medium, the Brassica tissue can be placed directly onto the medium or can be placed onto a filter film that is then placed in contact with the medium. When using liquid medium, the Brassica tissue can be placed onto a floatation device that contacts the liquid medium. A floatation device is typically a porous membrane as described elsewhere (U.S. Pat. No. 5,324,657). Examples of floatation devices, methods of using floatation devices, and accessory equipment that aids in liquid culture techniques are ready available from manufacturers such as Life Technologies (Rockville, Md.) and Osmotek Ltd. (Kiryat Weizmann Rehovot 76120, Israel). Typically, faster grown tissue is cultured on liquid medium. For example, liquid selection medium and liquid regeneration medium can be used to culture *Brassica juncea* tissue.

Nucleic Acid Molecules

Either circular or linear nucleic acid molecules can be used to coat particles that are, in turn, used to transform Brassica. In addition, these nucleic acid molecules can be RNA or DNA, including cDNA, genomic DNA, and synthetic (e.g., chemically synthesized) DNA, and can be double-stranded or single-stranded. Where single-stranded, the nucleic acid can be the sense strand or the anti-sense strand. Fragments of these molecules are also considered within the scope of the invention, and can be produced, for example, by polymerase chain reaction (PCR) or generated by treatment with one or more restriction endonucleases. RNA molecules can be produced, for example, by in vitro transcription.

The nucleic acid molecules of the invention typically encode a polypeptide or regulate the expression of a polypeptide. For example, a cDNA that encodes an enzyme or an anti-sense molecule that prevents an enzyme from being made can be used. The term "anti-sense molecule" encompasses any nucleic acid molecule that contains sequences that are complementary to the coding strand of a naturally-occurring polypeptide. An anti-sense molecule can also include flanking sequences, e.g., regulatory sequences, or introns. Thus, enzymatic nucleic acid molecules that specifically target and cleave RNA by using complementary anti-sense sequences such as ribozymes as well as anti-sense oligonucleotides are considered anti-sense molecules within the scope of the invention. These ribozymes can have any general structure including, without limitation, hairpin, hammerhead, or axhead structures, provided the molecule cleaves RNA.

Generally, a nucleic acid molecule of the invention is in the form of a plasmid and contains sequences that encode a polypeptide as well as promote the expression of the polypeptide when present in a Brassica cell. The sequences that promote polypeptide expression are typically regulatory sequences that flank the polypeptide encoding sequences. A polypeptide can be any synthetically engineered or biologically derived polypeptide. In addition, the polypeptide can be naturally occurring in Brassica or heterologous to Brassicca. Thus, Brassica polypeptides, plant polypeptides, non-plant polypeptides, modified polypeptides, synthetic polypeptides, and portions of polypeptides are considered within the scope of the invention.

The compositions of, and methods of constructing, nucleic acid molecules for successful transformation of plants are well known to those skilled in the art. For example, the uses of suitable nucleic acid components such as promoters, polyadenylation sequences, selectable marker sequences, reporter sequences, enhancers, introns, and the like as well as references providing the specific compositions of those components are described elsewhere (Weising et al., *Ann. Rev. Genetics* 22:421–478 (1988)). In addition, suitable methods of construction are described elsewhere (Sambrook J., et al., Molecular Cloning: A Laboratory Manual, 2nd ed., Cold Spring Harbor Laboratory Press (1989)). It is important to note that the same or similar compositions and methods can be used herein to produce nucleic acid molecules that are useful for transforming Brassica since the specific composition of the nucleic acid molecule used to transform Brassica is not central to the present invention and the invention is not dependent upon the composition of the specific transforming nucleic acid molecule used.

Nucleic acid molecules that are particularly useful for transforming Brassica include DNA molecules that provide for, or enhance, a beneficial feature of the resultant transformed Brassica plant. For example, the DNA can encode polypeptides or anti-sense molecules that promote increased food values, higher yields, pest resistance, disease resistance, and the like. Specific examples include, without limitation, a heterologous fatty acid desaturase or fatty acid elongase that alters fatty acid composition, a Bt-endotoxin gene or protease inhibitor that confers insect resistance; a bacterial ESPS synthase gene that confers resistance to glyphosate herbicide; and a chitinase or glucan endo-1,3-B-glucosidase gene that confers fungicidal properties. In addition, the nucleic acid molecule can be introduced into Brassica to act as a genetic tool to generate mutants and/or assist in the identification, genetic tagging, or isolation of segments of Brassica DNA. Additional nucleic acid molecules that provide a beneficial feature or are useful as a genetic tool are commonly known to the skilled artisan and are considered within the scope of the invention.

The nucleic acid molecule introduced into Brassica can also contain nucleic acid sequences that encode a selectable marker, a reporter, or both. The expression of these sequences in Brassica can facilitate the identification and selection of cells transformed stably, transiently, or both. Alternatively, the selectable marker can be carried on a separate nucleic acid molecule that is introduced using a cotransformation procedure. The sequences encoding these selectable markers and reporters can be flanked with appropriate regulatory sequences that facilitate expression in Brassica. Useful selectable markers are well known in the art and include, for example, antibiotic and herbicide resistance genes. Specific examples of such genes are disclosed elsewhere (Weising et al., *Ann. Rev. Genetics* 22:421–478 (1988)). A typical selectable marker gene is the aminoglycoside phosphotransferase gene of transposon Tn5 (AphII) that encodes a polypeptide that confers resistance to the antibiotics kanamycin, neomycin, and G418 (geneticin). Other selectable markers known in the art include the hygromycin B phosphotransferase (HPT) coding sequence that can be derived from *E. coli* as well as those genes that encode polypeptides that confer resistance or tolerance to glyphosate, methotrexate, phosphinothricin, imidazolinones, sulfonylureas, bromoxynil, dalapon, and the like. The expression of selectable marker genes that confer herbicide resistance or tolerance in transformed Brassica plants are commercially useful.

Reporter genes that encode easily assayable marker polypeptides are well known in the art. In general, a reporter gene is a gene that is not present or expressed by the recipient organism or tissue and that encodes a polypeptide whose expression is manifested by some easily detectable property, e.g. phenotypic change or enzymatic activity. Examples of such reporters are provided elsewhere (Weising et al., *Ann. Rev. Genetics* 22:421–478 (1988)). Typical reporters include the green fluorescent protein (GFP) gene from the bioluminescent jellyfish *Aequorea victoria*, variants of GFP, chloramphenicol acetyl transferase gene from Tn9 of *E. Coli*, beta-glucuronidase gene of the uidA locus of *E. Coli*, and luciferase genes from the firefly *Photinus pyralis*. Vectors containing GFP and GFP variant nucleic acid sequences are available commercially from Clontech Laboratories, Inc. (Palo Alto, Calif.). GFP Application Notes (Living Colors™; PT2040-1; Clontech Laboratories, Inc.) describes both GFP and GFP variants.

The regulatory sequences useful herein include any constitutive, inducible, tissue or organ specific, or developmental stage specific promoters that operate in plant cells. Suitable such promoters are disclosed elsewhere (Weising et al., *Ann. Rev. Genetics* 22:421–478 (1988)). The following is a partial representative list of promoters suitable for use herein: regulatory sequences from the T-DNA of *Agrobacterium tumefaciens*, including mannopine synthase, nopaline synthase, and octopine synthase; alcohol dehydrogenase promoter from corn; light inducible promoters such as the ribulose-biphosphate-carboxylase small subunit gene from a variety of species; the major chlorophyll a/b binding protein gene promoter; 35S and 19S promoters of cauliflower mosaic virus; developmentally regulated promoters such as oleosin, cruciferin, napin, and phaseolin promoters; as well as synthetic or other natural promoters that are either inducible or constitutive, including those promoters exhibiting organ specific expression or expression at specific developmental stage(s) of the plant.

Particularly, preferred promoters are those that allow seed-specific expression. Such promotes useful since seeds are the primary source of vegetable oils and also since seed-specific expression will avoid any potential deleterious effect in non-seed tissues. Examples of seed-specific promoters include, but are not limited to, the promoters of seed storage proteins, which can represent up to 90% of total seed protein in many plants. The seed storage proteins are strictly regulated, being expressed almost exclusively in seeds in a highly tissue-specific and stage-specific manner (Higgins et al., *Ann. Rev. Plant Physiol.* 35:191–221 (1984); Goldberg et al., *Cell* 56:149–160 (1989)). Moreover, different seed storage proteins may be expressed at different stages of seed development.

Expression of seed-specific genes has been studied in great detail (See reviews by Goldberg et al., *Cell* 56:149–160 (1989)) and Higgins et al., *Ann. Rev. Plant Physiol.* 35:191–221 (1984)). There are currently numerous examples of seed-specific expression of seed storage protein genes in transgenic dicotyledonous plants.

Other examples of seed-specific promoters are from genes expressed during early embryogenesis and oil biosynthesis. For example, native regulatory sequences, including the native promoters, of fatty acid desaturase genes can be used following their isolation by those skilled in the art. Heterologous promoters from other genes involved in seed oil biosynthesis, such as those for *Brassica napus* isocitrate lyase and malate synthase (Comai et al., *Plant Cell* 1:293–300 (1989)), delta-9 desaturase from safflower (Thompson et al., *Proc. Natl. Acad. Sci. USA* 88:2578–2582 (1991)) and castor (Shanklin et al., *Proc. Natl. Acad. Sci. USA* 88:2510–2514 (1991)), acyl carrier protein (ACP) from Arabidopsis (Post-Beittenmiller et al., *Nucl. Acids Res.* (1989) 17:1777), *Brassica napus* (Safford et al., *Eur. J. Biochem.* 174:287–295 (1988)), and *Brassica campestris*

(Rose et al., *Nucl. Acids Res.* 15:7197 (1987)), β-ketoacyl-ACP synthetase from barley (Siggaard-Andersen et al., *Proc. Natl. Acad. Sci. USA* 88:4114–4118 (1991)), and oleosin from *Zea mays* (Lee et al., *Proc. Natl. Acad. Sci. USA* 88:6181–6185 (1991)), soybean (Genbank Accession No: X60773) and *Brassica napus* (Lee et al., *Plant Physiol.* 96:1395–1397 (1991)) will be of use.

A nucleic acid molecule can also contain other elements such as introns, enhancers, polyadenylation sequences and the like. Such elements may or may not be necessary for the function of the nucleic acid molecule, although they can provide better expression or functioning of the nucleic acid molecule by affecting transcription, stability of the mRNA, or the like. Such elements can be included in the nucleic acid molecule as desired to obtain the optimal performance of the transforming nucleic acid in the plant. Sufficient expression, however, for a selectable marker to perform satisfactorily can often be obtained without an intron.

To determine if a particular combination of nucleic acid components functions as desired, Brassica recipient cells can be stably or transiently transformed by particle bombardment with a nucleic acid molecule construct that contains both that particular combination is well as a reporter. At a suitable time after transformation, an assay for expression of the reporter can be performed. One assay, for example, entails identifying the transient expression of the *E. Coli* beta-glucuronidase (GUS) gene (Jefferson et al., *EMBO J.* 6:3901–3907 (1987)). In this case, a suitable time for conducting the assay is about 1–3 days after bombardment. The use of transient assays is particularly important when using a nucleic acid molecule that contains components that have not previously been demonstrated or confirmed as compatible with the desired Brassica recipient cells.

Particle Bombardment

The nucleic acid molecules described herein are introduced into non-embryo Brassica tissue preparations using a particle bombardment process. General descriptions of suitable particle bombardment instruments and particle bombardment methods are provided elsewhere (Sanford et al., *J. Part. Sci. Technol.* 5:27–37 (1987)); Heiser W., "Optimization of Biolistic® transformation using the helium-driven PDS-1000/He system" in US/EG Bulletin 1688, BIO-RAD; and Dunder et al., "Comparison of performance characteristics of different Biolistic® devices" in US/EG Bulletin 1689, BIO-RAD). Briefly, the particle bombardment process, also referred to as a biolistic process, delivers a desired nucleic acid molecule to a cell by using very small particles, made from a biologically inert material, that have been coated with a nucleic acid molecule. When the inert particles are coated with the nucleic acid molecule and accelerated to a suitable velocity, one or more of the particles enter into one or more of the cells, with the nucleic acid molecule being released from the particle and expressed within the cell. While some of the cells may be fatally damaged by the bombardment process, others survive. Some of the recipient cells that survive stably retain the introduced nucleic acid molecule and express it.

The particles, called microprojectiles, are generally of a high density material such as tungsten or gold. They are coated with the nucleic acid molecule of interest. Coating procedures have been described in detail elsewhere (Stanford et al., *Methods Enzymol.* 217:483–509 (1993) and Heiser W., "Optimization of Biolistic® transformation using the helium-driven PDS-1000/He system" in US/EG Bulletin 1688, BIO-RAD). The microprojectiles are then placed onto the surface of a macroprojectile that serves to transfer the motive force from a suitable energy source to the microprojectiles. After the macroprojectile and the microprojectiles are accelerated to the proper velocity, they contact a blocking device that prevents the macroprojectile from continuing its forward path but allows the nucleic acid molecule-coated microprojectiles to continue on and impact the recipient Brassica cells. Suitable instruments can use a variety of motive forces such as a high pressure helium tank, gunpowder, and shock waves from an electric arc discharge (Sanford et al., *J. Part. Sci. Technol.* 5:27–37 (1987) and Sanford et al., *Technique* 3:3–16 (1988)).

A protocol for the use of a gunpowder instrument is provided by Klein T et al. (*Proc. Natl. Acad. Sci. U.S.A.* 85:4305–4309 (1988) and *Bio/Technology* 6:599–563 (1988)) and involves two major steps. First, tungsten microprojectiles are coated when mixed with the nucleic acid molecule, calcium chloride, and spermidine free-base in a specified order in an aqueous solution. The concentrations of the various components can be varied. For example, any concentration of the nucleic acid molecule can be used provided the recipient Brassica cells express the transferred nucleic acid molecule. Second, in the actual bombardment, both the distance of the recipient cells from the end of the barrel and the vacuum in the sample chamber are set. These settings are also described elsewhere (Klein et al., *Bio/Technology* 6:599–563 (1988)) and can be varied.

A protocol for the use of a high pressure helium tank instrument (Biolistic® PDS-1000/He Particle Delivery System) is provided by the manufacture (BIO-RAD, Hercules Calif.). Specific conditions such as the concentration of the nucleic acid molecule used to coat microprojectiles, the helium pressure used to accelerate the microprojectiles, and the distance of the stopping screen from the sample, can be varied. Typically, the recipient tissue is positioned about 6 to 9 cm below the stopping plate tray.

The specific Brassica tissue preparations described herein can be placed on a petri dish or other surface and arranged in essentially any manner, recognizing that (I) the area in the center of the dish may receive the heaviest concentration of nucleic acid molecule-coated particles and the tissue located there may suffer damage during bombardment and (ii) the number of particles reaching a cell may decrease as the distance of the cell from the center of the blast area increases such that cells far from the center of the dish may not be bombarded and transformed. The Biolistic® PDS-1000/He Particle Delivery System (BIO-RAD, Hercules Calif.) can deliver a more even distribution of microprojectiles to recipient cells. A mesh screen, preferably of metal, optionally can be laid on the dish to prevent splashing or ejection of the tissue. The tissue can be bombarded one or more times with the nucleic acid molecule-coated particles. In addition, cells can be bombarded with particles coated with a single type of nucleic acid molecule or multiple different nucleic acid molecules. Likewise, a tissue preparation can be bombarded with a collection of particles wherein the collection contains different sets each coated with a different nucleic acid molecule.

Identifying Transformed Brassica

Once the Brassica tissue preparation has been bombarded with the coated particles and the nucleic acid molecule has penetrated some of the cells, it is necessary to identify cells that both contain the nucleic acid molecule and retain sufficient regenerative capacity. Many approaches can be used to identify transformed plant cells and are known to those skilled in the art. Briefly, two general approaches found to be useful are described. First, transformed Brassica cells or plants regenerated from them can be screened for the presence of the nucleic acid molecule by various standard methods including, without limitation, assays for the expression of a reporter contained within the nucleic acid molecule and assessments of phenotypic effects caused by the expression of the nucleic acid molecule, if any. Second, a selectable marker sequence can be transmitted along with or as part of the nucleic acid molecule. In this case, transformed cells can be identified by the use of a selective agent to detect expression of the selectable marker.

Selection conditions must be chosen so as to allow growth and accumulation of transformed cells while simultaneously inhibiting the growth of non-transformed cells. This situation can be complicated by the fact that the vitality of individual cells in a population is often highly dependent on the vitality of neighboring cells. In addition, selection conditions must not be so severe that the plant regenerating capacity of transformed cells and the fertility of the resulting plant are precluded. Thus, the effects of the selection agent on cell viability and morphology should be evaluated. This can be accomplished beforehand by experimentally producing a growth inhibition curve for a given selective agent and tissue, thereby establishing the concentration range that does not inhibit growth.

When using a selectable marker, the bombarded Brassica tissue can be either allowed to recover from the bombardment on non-selective medium or directly transferred to medium containing the selection agent.

Selection procedures typically involve exposing the bombarded tissue to a toxic agent. The tissue can be subjected to sequential changes in the concentration of the agent as well as multiple rounds of selection. The particular concentrations and cycle lengths typically vary depending on the particular agent used. In addition, the selection procedure can involve using an initial selection round at a relatively low toxic agent concentration and then later round(s) at higher concentration(s). This allows the selective agent to exert its toxic effect slowly over a longer period of time. Initially, the concentration of the agent can be such that about a 5–40% level of growth inhibition occurs, as determined from a growth inhibition curve. The goal is to allow transformed cells to grow and divide preferentially while inhibiting untransformed cells, but not to the extent that growth of transformed cells is prevented. Once a few individual transformed cells have grown sufficiently, the tissue can be shifted to media containing a higher concentration of the toxic agent to kill essentially all untransformed cells. The shift to higher concentrations also reduces the possibility of non-transformed cells habituating to the agent. A higher concentration can be a concentration that inhibits about 30 to 100% growth. The length of the first selection cycle can be from about 1 to 4 weeks, typically about 2 weeks. Later selection cycles can be from about 1 to about 12 weeks, typically about 2 to about 10 weeks. Putative Brassica transformants generally can be identified as proliferating sectors of tissue or cells against a background of non-proliferating cells. The bombarded Brassica tissue can also be cultured on non-selective media at various times during the overall selection procedure.

Once a sector is identified as a putative transformant, transformation can be confirmed by phenotypic and/or genotypic analysis. If a selection agent is used, an example of phenotypic analysis can include measuring any increase in fresh weight of the putative transformant as compared to a control on various levels of the selective agent. Other analyses that can be used will depend on the function of the transferred nucleic acid molecule. For example, if an enzyme or other polypeptide is encoded by the nucleic acid molecule, then enzymatic or immunological assays specific for that particular enzyme or polypeptide can be used. Specific bioassay and chemical assay techniques that are suitable for detecting the expression of transferred nucleic acid molecules are well known in the art and are not repeated here. The presence of the nucleic acid itself can also be confirmed by conventional procedures, i.e. Southern blot, Northern blot, or PCR analysis or the like.

Regeneration of Brassica Plants

Transformed Brassica cells can be regenerated into plants and the fertility of the resultant plants determined. Briefly, cells that test positive for transformation are placed on medium that promotes tissue differentiation and plant regeneration. An example of a regeneration medium includes, without limitation, MS medium containing relatively lower concentrations of auxin, e.g., indole-3-acetic acid (IAA), and relatively higher concentrations of cytokinin, e.g., zeatin. The specific regeneration process can be carried out in accordance with standard procedures well known in the art. Typically, these procedures entail reducing the level of auxin. The regenerating medium can also contain the same selection agent used in the selection medium. The regenerated plants can be grown to maturity in a growth room or greenhouse and appropriate sexual crosses and selfs made.

It is important to note that plant regeneration, while important to the present invention, can be performed in any conventional manner. For example, if a selectable marker has been introduced into the cells, then a selection agent can be incorporated into the regeneration medium to further confirm that the regenerated plantlets are transformed. Since regeneration techniques are well known and not critical to the present invention, any technique that accomplishes regeneration and produces fertile plants can be used.

Analysis of Progeny

The plants regenerated from transformed Brassica are referred to as the $R_0$ generation or $R_0$ plants. The seeds produced by various sexual crosses of $R_0$ generation plants are referred to as $R_1$ progeny or $R_1$ generations. When $R_1$ seeds are germinated, the resulting plants are also referred to as the $R_1$ generation.

The $R_1$ generation should be analyzed to confirm successful transmission and inheritance of the transferred nucleic acid molecule. The analysis can be performed using any of the methods described herein to identify transformants taking into account that any portion of the plant can be used. Further, any $R_1$ or later (e.g., $R_2$, $R_3$, $R_4$, and etc.) plants as well as $F_1$ or later (e.g., $F_2$, $F_3$, $F_4$, and etc.) plants can be analyzed.

It is apparent from the above that the term progeny includes descendants of a particular cell, cell line, plant, or plant line, e.g., seeds developed on a plant and plants derived from such seeds. Progeny of a plant include seeds formed on $R_0$, $R_1$, $R_2$ and subsequent generation plants, seeds formed on $F_1$, $F_2$, $F_3$, and subsequent generation plants, or seeds formed on $BC_1$, $BC_2$, $BC_3$ and subsequent generation plants. Thus, selfed progeny includes not only the $R_1$ progeny of the initial self-pollination, but also $R_2$, $R_3$, and subsequent generations.

Breeding Transgenic Brassica

Generally, commercial value of transformed Brassica plants produced herein will be greatest if the nucleic acid molecule can be incorporated into many different varieties. A farmer typically grows several varieties based on differences in maturity, standability, and other agronomic traits. Also, the farmer must select a variety based upon geographic location since varieties adapted to a specific growing environment are generally not adapted to another because of differences in such traits as maturity, disease, and insect resistance. As such, it can be advantageous to incorporate the nucleic acid molecule into a large number of parental Brassica lines so that many varieties can be produced containing the desired nucleic acid molecule. This can conveniently be done by breeding programs in which a conversion process (back crossing) is performed by crossing the initial transgenic fertile plant to normal elite inbred lines and then crossing the progeny back to the normal parent. The progeny from this cross will segregate such that some of the plants will carry the nucleic acid molecule whereas some will not. The plants that do carry the nucleic acid molecule are then crossed again to the normal plant resulting in progeny that segregate once more. This crossing is repeated until the original normal parent has been converted to a genetically engineered line containing the nucleic acid molecule and also possessing all other important attributes originally found in the parent. A separate backcrossing program can be used for every elite line that is to be converted to a genetically engineered elite line. It may be necessary for both parents to be homozygous for the nucleic acid molecule. Brassica breeding and the techniques and skills required to transfer genes from one line or variety to another are well-known to those skilled in the art.

Uses of Transgenic Brassica Plants

Transgenic plants produced as described herein are useful for a variety of commercial and research purposes. Transgenic plants can be created for use in traditional agriculture to possess traits beneficial to the grower (e.g. agronomic traits such as pest resistance or increased yield), beneficial to the consumer of the product harvested from the plant (e.g. improved nutritive content in human food or animal feed), or beneficial to the food processor (e.g. improved processing traits). Chemical constituents such as oils and starches of Brassica can be extracted for food or industrial use and transgenic plants can be created to enhance or modify the levels of such components. The plants can also be used for seed production for a variety of purposes.

Transgenic plants can also find use in the commercial manufacture of polypeptides or other molecules encoded by the nucleic acid molecule contained therein, where the expressed molecule of interest is extracted or purified from plant parts, seeds, and the like. In addition, cells or tissue from transgenic plants can be cultured, grown in vitro, or fermented to manufacture the desired molecules or for other purposes such as research.

The transgenic plants can also be used in commercial breeding programs or can be crossed or bred to plants of related crop species. Improvements encoded by the nucleic acid molecule can be transferred from one Brassica species to another Brassica species by, for example, protoplast fusion.

Transgenic plants can have many uses in research or breeding, including creation of new mutant plants through insertional mutagenesis, in order to identify beneficial mutants that might later be created by traditional mutation and selection. The methods of the invention can also be used to create plants having unique "signature sequences" or other marker sequences that can be used to identify proprietary lines or varieties.

The invention will be further described in the following examples, which do not limit the scope of the invention described in the claims.

EXAMPLES

Transformed Brassica plants were generated by particle bombardment using specific tissue preparation procedures.

Example 1

Brassica Transformation Using a Slicing Tissue Preparation Method

Sterilized seeds of Brassica napus variety Westar were grown on MS medium with agar and 30 mM $CaCl_2$ to germinate in the dark for 5–6 days. Seedlings at this stage were 3–6 cm in height with shoot tips. The advantage of using sterile seedlings as a tissue source is that it requires minimal facility, time, and effort to maintain the donor materials. The hypocotyls of these seedlings were harvested and cut into pieces 2–3 cm in length. Each hypocotyl piece was sliced longitudinally into two halves and then placed on induction medium with the epidermal side in contact with the medium, i.e., the freshly cut surface was facing generally upward. The induction medium was MS medium with 0.5 to 1.0 mg/liter 2,4-dichlorophenoxy acetic acid (2,4-D) and 0.2 to 0.3 mg/liter kinetin. The longitudinal slices were arranged tightly together with about 20 pieces per dish. After being cultured for 1–2 days on induction medium, the longitudinal slices were bombarded with nucleic acid-coated gold particles.

The nucleic acid molecule used to coat particles for the bombardment and transformation of the non-embryo Brassica cells was pIMC38 (FIG. 1). This construct contains two genes: neomycin phosphotransferase (NPTII) gene and beta-glucuronidase (GUS) gene. Both genes were driven by a CaMV 35S promoter and terminated with a nopaline synthase (NOS) gene terminator. The 35S-NPTII-NOS and 35S-GUS-NOS units were arranged in opposite directions. The NPTII gene served as a selection marker that, if properly expressed, confers resistance to kanamycin on transferred cells in culture and renders transformed seeds resistant to geneticin during germination.

The apparatus used to bombard non-embryo Brassica cell or tissue preparations was a Biolistic® PDS-1000/He System (Dupont). The procedure for the particle bombardment followed the BioRad: US/EG Bulletin 1688 and 1689. The specific metal particles used were $0.6\mu$ or $1.0\mu$ gold particles.

After being bombarded, the longitudinal slices were cultured in induction medium for 3 days. The cultures then were transferred to selection medium. The selection medium was the same as the induction medium except that the selection agent kanamycin was added to a final concentration of 25 mg/liter. After 2–3 weeks, the cultures were transferred to regeneration medium, which contained 2 mg/liter zeatin, 0.1 mg/liter IAA, and 25 mg/liter kanamycin. These cells were sub-cultured on the regeneration medium about every two weeks thereafter until green shoots appeared.

One of the regenerated plants was selected (named "Peter") and analyzed for the presence of NPTII nucleic acid. Specifically, leaf tissue was collected from "Peter" and DNA was extracted from those cells and analyzed by PCR using NPTII specific primers. This analysis revealed that cells from "Peter" contained NPTII nucleic acid (Table I).

Regenerated plants were grown in a green house to sexual maturity. Controlled pollination was carried out between "Peter" and a non-transgenic commercial B. napus variety Quantum. "Peter" was also self-pollinated.

$R_1$ seeds were harvested from "Peter" and $F_1$ seeds were harvested from the Quantum X "Peter" cross, and tested for geneticin resistance. Sterilized seeds were placed into test medium that contained 1.2 g/liter bacto-agar and 50 mg/liter or 100 mg/liter geneticin (Gibco-LifeSciences, I1811-023). The seeds were pushed into the medium about 0.1 to 0.4 cm in depth after which the germination status was measured weekly with a final score being recorded after three weeks. The following descriptions were used to score the germination status of the seeds. Typically, when grown in 50 mg/liter geneticin test medium, non-transgenic seeds grow up to 1.5 cm in height, and have cotyledons that are green with yellow to brown colored edges, but roots will not be more than 0.5 cm in length. In addition, non-transgenic seeds will not grow into viable seedlings after staying in the 50 mg/liter geneticin test medium for two weeks. Thus, seeds that germinate into seedlings with green cotyledons having a height greater than 2 cm and roots longer than 1 cm in 50 mg/liter geneticin test medium were defined as NPTII positive. In addition, seeds that germinated in 50 mg/liter geneticin medium as quickly and normally as non-transgenic seeds grown in geneticin-free medium were marked as "++".

TABLE I

Analysis of regenerated plant "Peter", selfed progeny, and $F_1$ crossed progeny.

| Plant Generation | PCR (NPTII) | Seed Germination on Geneticin-containing Medium |
| --- | --- | --- |
| $R_0$ | positive | N/A |
| $R_1$ | not tested | ++ |
| $F_1$ | not tested | + |
| $R_2$ | not tested | ++ |
| $F_2$ | not tested | ++ |

++ = normal vigor, normal plantlet morphology;
+ = moderate vigor, normal plantlet morphology;
N/A = not applicable Some $R_1$ seeds from the regenerated plant "Peter" ($R_0$) germinated normally when grown on geneticin-containing medium, indicating the transformation of Brassica (Table I). Some $R_1$ seedlings that survived the geneticin selection were transferred to soil, self-pollinated, and $R_2$ seeds harvested. Most of these $R_2$ seeds germinated and grew on geneticin-containing medium normally and vigorously. $F_1$ seeds that germinated on geneticin-containing medium were not as vigorous as the geneticin-resistant $R_1$ or $R_2$ seeds. Thus, NPTII copy number and the homozygous nature of the integrated NPTII nucleic acid appeared to affect the level of NPTII expression. Some $F_1$ seedlings that survived the geneticin selection were transferred to soil self-pollinated and $F_2$ seeds were harvested. About half of these $F_2$ seeds germinated and grew on geneticin-containing medium normally and vigorously.

Example 2

Brassica Transformation Using a Grinding Tissue Preparation Method

Four to six day old sterile seedlings of Brassica napus variety Westar were harvested and the lower portion of the hypocotyls, seed coat, and roots were discarded. The remaining upper portion of the seedling contained 10%–50% of the hypocotyl, two cotyledons, and a shoot tip. This upper portion was ground with liquid induction medium into a cellular slurry using a blender. Specifically, the upper portion from about 200 seedlings was mixed with 30 ml of induction medium. This mixture was macerated in a blender (Blender Model 33BL79, Warning Products Division, Dynamics Corporation of America) at room temperature. The resulting slurry was sorted through a series of meshes into groups having different ranges of tissue sizes. The group with a tissue size of 46–230 microns was collected and cultured at high density on 12 filter films (4 cm diameter) that had been placed on solid induction medium. After 3 days of culture, films containing ground tissue were bombarded with nucleic acid molecule-coated gold particles as described in Example 1 and cultured on induction medium for another 3 days. The cultures then were transferred to selection medium for 2–3 weeks followed by culturing on regenerating medium until shoots were regenerated.

Regenerated plants were analyzed for the presence NPTII nucleic acid as described in Example 1. In addition, portions of such plants were analyzed for GUS expression. Briefly, cells that express GUS appear blue following a GUS staining assay. The GUS staining assay used was described in detail by Anne-Marie Stopm in Sean R. Gallagher (ed.), *GUS Protocols: Using the GUS Gene as a Reporter of Gene Expression*, pp. 103–113, Academic Press, San Diego, Calif., 1992. Some regenerated shoots and leaves showed strong blue color after GUS staining, indicating the expression of the transferred foreign GUS nucleic acid sequences.

The regenerated plants were transferred to soil and grown to maturity. Ten $R_1$ seeds were tested for geneticin resistance by the seed germination test described in Example 1. Six failed to germinate. Two of the four remaining seeds were geneticin resistance and the resulting plantlets exhibited moderate vigor under such conditions (Table II). In addition, 17 $R_1$ seeds were germinated in the absence of geneticin and a leaf piece of each seedling was stained for GUS as described above. Eleven of these exhibited strong blue color (Table II). Taken together, these results indicate that both the NPTII gene and the GUS gene were integrated into the genome and successfully transmitted to the progeny.

TABLE II

Analysis of regenerated plants created using the grinding method

| Plant Generation | GUS Staining | Germination on Geneticin-containing Medium |
| --- | --- | --- |
| $R_0$ | positive | N/A |
| $R_1$ | positive | + |

+ = moderate vigor, normal plantlet morphology;
N/A = not applicable

Example 3

Transformation of Brassica juncea

Brassica juncea line DZJ-01 is a proprietary line that has tissue culture and regeneration characteristics comparable to those of other Brassica juncea lines. Line DZJ-01 was successfully transformed using the grinding tissue preparation method described in Example 2. Because DZJ-01 tissue grew more rapidly in culture than Brassica napus tissue, some culture conditions were modified. Specifically, DZJ-01 tissue was prepared and bombarded as described in Example 2. After bombardment, the tissue was grown on solid induction medium for six days. Cultures were then transferred to a floating raft system and cultured in a liquid selection medium for eight days, at which time the medium was changed to liquid regeneration medium. These two liquid media had the same composition as the corresponding media as in Example 2 except that agar was omitted. The floating raft system included a LifeRaft Membrane Raft (Life Technologies, Cat. No. 10518-017), a LifeRaft Float Unit (Life Technologies Cat. No. 10521-011), and a Magenta vessel with LifeGuard Membrane Vented Lid (Life Technologies Cat. No. 10678-019) and was used as described by the manufacturer.

The regeneration medium was renewed every week until green shoot tips developed. After shoots had formed, they were transferred to solid regeneration medium and then transferred to solid hormone-free MS medium.

One of the regenerated plants (named "J.J.") exhibited a strong blue color in the GUS staining assay described above. In addition, PCR analysis using GUS-specific primers revealed strong positive signals indicating that GUS specific sequences were present (Table III). Taken together, these results suggest that the introduced DNA was integrated into the genome of the $R_0$ plant. At sexual maturity, "J.J." was self-pollinated and $R_1$ seeds were harvested. To verify integration, $R_1$ seeds were germinated and the resulting plantlets were tested for GUS expression. Some of the $R_1$ seedlings exhibited strong blue color after GUS staining, indicating the integration of the GUS gene into the *Brassica juncea* genome.

TABLE III

Analysis of regenerated *Brassica juncea* plants

| Plant Generation | GUS Staining | PCR (GUS) |
| --- | --- | --- |
| $R_0$ | positive | positive |
| $R_1$ | positive | not tested |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of producing one or more transformed Brassica cells, said method comprising the steps of:
   (a) bombarding cells prepared from non-embryo Brassica tissue with microprojectiles coated with nucleic acid to form a bombarded cell preparation; and
   (b) identifying one or more cells of said bombarded preparation that have been stably transformed with said nucleic acid, wherein said one or more identified cells are said transformed Brassica cells.

2. The method of claim 1, wherein said cells prepared from non-embryo Brassica tissue are diploid.

3. The method of claim 1, wherein said non-embryo Brassica tissue is from a Brassica seedling.

4. The method of claim 3, wherein said seedling is a 4–6 day old sterile seedling.

5. The method of claim 1, wherein said cells being bombarded are prepared from non-embryo Brassica tissue by cutting said tissue into at least one piece and contacting said at least one piece with induction medium.

6. The method of claim 1, wherein said cells being bombarded are prepared from non-embryo Brassica tissue by cutting a hypocotyl from a seedling in a generally transverse orientation to form at least one hypocotyl piece, slicing said at least one hypocotyl piece longitudinally, and contacting at least one of said longitudinal slices with induction medium.

7. The method of claim 1, wherein said cells being bombarded are prepared from non-embryo Brassica tissue by macerating said tissue into a cellular slurry.

8. The method of claim 1, wherein said cells being bombarded are prepared from non-embryo Brassica tissue by macerating the upper portion of a seedling in induction medium to form a cellular slurry, said upper portion comprising the shoot tip, cotyledons, and 10–50 percent of the hypocotyl.

9. The method of claim 7, wherein said cellular slurry is enriched for cellular matter having a size of about 46 microns to about 230 microns.

10. The method of claim 1, wherein said nucleic acid encodes a polypeptide or regulates the expression of a polypeptide.

11. The method of claim 1, wherein said nucleic acid comprises an anti-sense molecule.

12. The method of claim 1, wherein said nucleic acid comprises a ribozyme.

13. The method of claim 1, wherein said nucleic acid comprises an anti-sense oligonucleotide.

14. The method of claim 1, wherein said Brassica tissue is from a Brassica species selected from the group consisting of *Brassica napus, Brassica juncea, Brassica carinata, Brassica nigra, Brassica oleracea*, and *Brassica campestris*.

15. The method of claim 1, wherein said identification comprises culturing said bombarded cells on a floatation device in contact with a liquid selection medium, and selecting one or more cells that survive in the presence of said selection medium.

16. The method of claim 1, wherein said method further comprises the step of regenerating a Brassica plant from said one or more identified cells.

17. The method of claim 16, wherein said regeneration comprises culturing said one or more identified cells on a floatation device in contact with liquid regeneration medium.

18. A transgenic Brassica cell or progeny thereof, wherein said transgenic Brassica cell is produced according to a transformation method, said method comprising:
   (a) bombarding cells prepared from non-embryo Brassica tissue with microprojectiles coated with nucleic acid to form a bombarded cell preparation; and
   (b) identifying a cell of said bombarded preparation that has been stably transformed with said nucleic acid, wherein said nucleic acid lacks T-DNA borders and wherein said identified cell is said transgenic Brassica cell.

19. A method for producing a transgenic Brassica plant, said method comprising:
   (a) bombarding cells prepared from non-embryo Brassica tissue with microprojectiles coated with nucleic acid to form a bombarded cell preparation;
   (b) selecting one or more cells of said bombarded preparation that have been transformed with said nucleic acid; and
   (c) regenerating a Brassica plant from said one or more selected cells, wherein said regenerated Brassica plant is stably transformed with said nucleic acid.

20. The method of claim 19, wherein said cells prepared from non-embryo Brassica tissue are diploid.

21. The method of claim 19, wherein said non-embryo Brassica tissue is from a Brassica seedling.

22. The method of claim 19, wherein said cells being bombarded are prepared from non-embryo Brassica tissue by cutting said tissue into at least one piece and contacting said at least one piece with induction medium.

23. The method of claim 19, wherein said cells being bombarded are prepared from non-embryo Brassica tissue by cutting a hypocotyl from a seedling in a generally transverse orientation to form at least one hypocotyl piece, slicing said at least one hypocotyl piece longitudinally, and contacting at least one of said longitudinal slices with induction medium.

24. The method of claim 19, wherein said cells being bombarded are prepared from non-embryo Brassica tissue by macerating said tissue into a cellular slurry.

25. The method of claim 19, wherein said Brassica tissue is from a Brassica species selected from the group consisting of *Brassica napus, Brassica juncea, Brassica carinata, Brassica nigra, Brassica oleracea*, and *Brassica campestris*.

26. The method of claim 19, wherein said regeneration comprises culturing said one or more selected cells on a floatation device in contact with liquid regeneration medium.

27. A transgenic Brassica plant or progeny thereof, said transgenic plant produced according to a transformation method, said method comprising:

(a) bombarding cells prepared from non-embryo Brassica tissue with microprojectiles coated with nucleic acid to form a bombarded cell preparation, wherein said nucleic acid lacks T-DNA borders;

(b) selecting one or more cells of said bombarded preparation that have been transformed with said nucleic acid; and (c) regenerating a Brassica plant from said one or more selected cells, wherein said regenerated Brassica plant is stably transformed with said nucleic acid.

28. The method of claim 1, wherein said nucleic acid lacks T-DNA borders.

29. The method of claim 19, wherein said nucleic acid lacks T-DNA borders.

30. A transgenic Brassica plant, wherein said plant comprises an introduced nucleic acid lacking T-DNA borders.

* * * * *